United States Patent
Hirano et al.

(10) Patent No.: US 10,992,852 B2
(45) Date of Patent: Apr. 27, 2021

(54) MEDICAL OBSERVATION DEVICE AND CONTROL METHOD

(71) Applicants: Sony Corporation, Tokyo (JP); Sony Olympus Medical Solutions Inc., Tokyo (JP)

(72) Inventors: Hirotaka Hirano, Gifu (JP); Tatsuya Ibuka, Aichi (JP); Takahiro Yamamoto, Tokyo (JP)

(73) Assignees: SONY CORPORATION, Tokyo (JP); SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 16/333,235

(22) PCT Filed: Oct. 6, 2017

(86) PCT No.: PCT/JP2017/036494
§ 371 (c)(1),
(2) Date: Mar. 14, 2019

(87) PCT Pub. No.: WO2018/100885
PCT Pub. Date: Jun. 7, 2018

(65) Prior Publication Data
US 2019/0281227 A1    Sep. 12, 2019

(30) Foreign Application Priority Data
Dec. 1, 2016   (JP) .............................. JP2016-233974

(51) Int. Cl.
*G02B 21/00*   (2006.01)
*H04N 5/232*   (2006.01)
(Continued)

(52) U.S. Cl.
CPC ... *H04N 5/232125* (2018.08); *A61B 1/00009* (2013.01); *A61B 1/00149* (2013.01);
(Continued)

(58) Field of Classification Search
None
See application file for complete search history.

(56) References Cited

U.S. PATENT DOCUMENTS 5,422,673 A * 6/1995 Kondo ............... H04N 5/23293
                                                348/352
5,913,079 A * 6/1999 Aoyama ................... G02B 7/28
                                                396/121
(Continued)

FOREIGN PATENT DOCUMENTS

JP    5-127068 A    5/1993
JP    2006-122232 A    5/2006
(Continued)

OTHER PUBLICATIONS

International Search Report and Written Opinion dated Jan. 16, 2018 for PCT/JP2017/036494 filed on Oct. 6, 2017, 15 pages including English Translation.

*Primary Examiner* — Shadan E Haghani
(74) *Attorney, Agent, or Firm* — Xsensus, LLP

(57) ABSTRACT

[Object] To provide a medical observation device and a control method.
[Solution] Provided is a medical observation device including: an imaging optical system including an objective optical system that condenses light from a subject and two image-forming optical systems which have optical axes different from an optical axis of the objective optical system and which cause light condensed by the objective optical system to form an image; and a control unit configured to cause an autofocus operation to be executed by causing a focusing optical member included in the objective optical system to move.

7 Claims, 9 Drawing Sheets

(51) Int. Cl.
  *A61B 90/20* (2016.01)
  *A61B 1/04* (2006.01)
  *A61B 1/045* (2006.01)
  *G02B 21/02* (2006.01)
  *G02B 21/24* (2006.01)
  *A61B 1/00* (2006.01)
  *G02B 7/34* (2021.01)
  *H04N 5/225* (2006.01)
  *G02B 7/28* (2021.01)
  *G02B 21/22* (2006.01)
  *G03B 35/08* (2021.01)
  *G02B 23/24* (2006.01)

(52) U.S. Cl.
  CPC ...... *A61B 1/00188* (2013.01); *A61B 1/00193* (2013.01); *A61B 1/042* (2013.01); *A61B 1/045* (2013.01); *A61B 90/20* (2016.02); *G02B 7/28* (2013.01); *G02B 7/34* (2013.01); *G02B 21/00* (2013.01); *G02B 21/0012* (2013.01); *G02B 21/025* (2013.01); *G02B 21/22* (2013.01); *G02B 21/241* (2013.01); *G02B 21/244* (2013.01); *G03B 35/08* (2013.01); *H04N 5/225* (2013.01); *H04N 5/232* (2013.01); *H04N 5/23296* (2013.01); *G02B 23/2407* (2013.01)

(56) References Cited

U.S. PATENT DOCUMENTS

| | | | | |
|---|---|---|---|---|
| 7,474,844 B2 * | 1/2009 | Kokabu | ................ | G02B 7/102 |
| | | | | 348/240.99 |
| 8,125,542 B2 * | 2/2012 | Ishikawa | ................ | H04N 5/232 |
| | | | | 348/240.99 |
| 2001/0055150 A1 * | 12/2001 | Ito | ................ | A61B 90/36 |
| | | | | 359/363 |

FOREIGN PATENT DOCUMENTS

| | | |
|---|---|---|
| JP | 2006-218103 A | 8/2006 |
| JP | 2010-207460 A | 9/2010 |
| JP | 2015-126288 A | 7/2015 |

* cited by examiner

MEDICAL OBSERVATION DEVICE AND CONTROL METHOD

CROSS-REFERENCE TO RELATED APPLICATIONS

The present application is based on PCT filing PCT/JP2017/036494, filed Oct. 6, 2017 which claims priority to JP 2016-233974, filed Dec. 1, 2016, the entire contents of which are incorporated herein by reference.

TECHNICAL FIELD

The present disclosure relates to a medical observation device and a control method.

BACKGROUND ART

Recently, due to advancements in surgical techniques and surgical equipment, surgeries for performing various treatments (also called microsurgery) while observing an affected site with an observation device for medical use, such as a surgical microscope or an endoscope, are coming to be conducted frequently. Also, such observation devices for medical use are not limited to devices that enable optical observation of the affected area, and also include devices that display an image of the affected area captured by an imaging section (camera) or the like as an electronic image on a display such as a monitor.

In addition, when displaying, on a display, an image of an affected area captured by an imaging section of an observation device, the image often is displayed as a flat two-dimensional (2D) image. However, since a sense of perspective is difficult to obtain from a 2D image, and the relative distance between the affected area and a treatment tool may be difficult to grasp, in recent years, technology that displays a captured image of an affected area as a stereoscopic three-dimensional (3D) image has also been developed.

In this manner, in an observation device (hereinafter, sometimes referred to as a "stereoscopic observation device") that displays a captured image of an affected area as a stereoscopic 3D image, for example, images of the affected area (hereinafter, also referred to as "viewpoint images") are captured by a plurality of imaging sections from mutually different viewpoints. Then, by causing left and right eyes to observe viewpoint images captured by mutually different imaging sections, it becomes possible to cause a user to observe an image of the affected area as a stereoscopic 3D image that is based on a parallax between the viewpoint images.

For example, Patent Literature 1 discloses one example of a mechanism that captures a parallax image of a subject with multiple imaging units, and thereby cause a stereoscopic 3D image of the subject to be observed on the basis of the parallax image. Also, the stereoscopic observation device disclosed in Patent Literature 1 is provided with an imaging optical system that includes an objective optical system and two image-forming optical systems for the right eye and the left eye, which have a different optical axis than the optical axis of the objective optical system and which cause light condensed by the objective optical system to form an image.

CITATION LIST

Patent Literature

Patent Literature 1: JP 2015-126288A

DISCLOSURE OF INVENTION

Technical Problem

As above, in an observation device provided with an imaging optical system that includes a single objective lens and an optical system which has an optical axis different from the optical axis of the objective lens and which causes light condensed by the objective lens to form an image, there is a demand to realize an autofocus function.

Solution to Problem

According to the present disclosure, there is provided a medical observation device including: an imaging optical system including an objective optical system that condenses light from a subject and two image-forming optical systems which have optical axes different from an optical axis of the objective optical system and which cause light condensed by the objective optical system to form an image; and a control unit configured to cause an autofocus operation to be executed by causing a focusing optical member included in the objective optical system to move.

Also, according to the present disclosure, there is provided a control method, executed by a processor, that includes executing an autofocus operation by moving the focus lens in an imaging optical system that includes an imaging optical system that includes an objective optical system configured to condense light from a subject and two image-forming optical systems which have an optical axis different from the optical axis of the objective optical system and which cause light condensed by the objective optical system to form an image.

Advantageous Effects of Invention

According to the present disclosure as described above, in an observation device provided with an imaging optical system that includes a single objective lens and an optical system which has an optical axis different from the optical axis of the objective lens and which causes light condensed by the objective lens to form an image, it becomes possible to realize an autofocus function.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
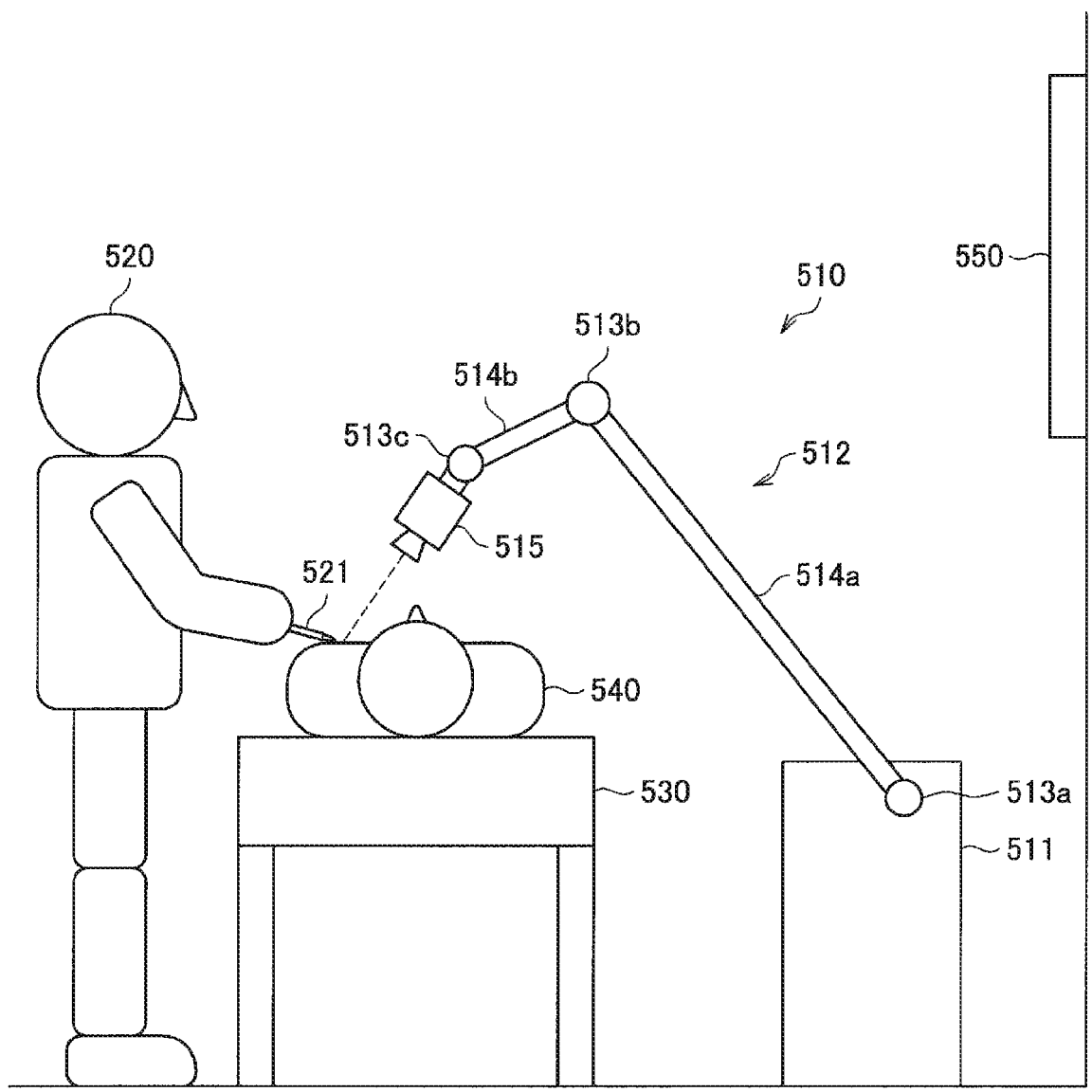
FIG. 1 is an explanatory diagram for explaining an applied example of a medical observation device according to one embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different alphabets after the same reference sign. However, when there is no need in particular to distinguish structural elements that have substantially the same function and structure, the same reference sign alone is attached.

Hereinafter, the description will proceed in the following order.

<<1. Overview>>
   <1-1. Applied example of medical observation device>
   <1-2. Exterior appearance of medical observation device>
   <1-3. Investigation of medical observation device>
<<2. Configuration>>
<<3. Operations>>
<<4. Modifications>>
   <4-1. Modification 1>
   <4-2. Modification 2>
<<5. Hardware configuration example>>
<<6. Conclusion>>

1. Overview

<1-1. Applied Example of Medical Observation Device>

First, to further elucidate the present disclosure, an applied example of a medical observation device according to an embodiment of the present disclosure will be described.

For example, FIG. 1 is an explanatory diagram for explaining an applied example of a medical observation device according to an embodiment of the present disclosure. FIG. 1 illustrates an example of a case for an applied example of using a medical observation device according to an embodiment of the present disclosure, in which a surgical video microscope device equipped with an arm is used as the medical observation device.

FIG. 1 diagrammatically illustrates how a medical procedure is performed using a surgical video microscope device according to the present embodiment. Specifically, referring to FIG. 1, a state is illustrated in which a physician acting as the surgeon (user) 520 is using a surgical tool 521, such as a scalpel, tweezers, or forceps, for example, to perform surgery on a subject (patient) 540 lying on an operating table 530. Note that in the following description, medical procedure is used as a collective term to denote various types of medical treatments performed by a physician acting as the user 520 on a patient acting as the subject 540, such as a surgery or an examination. Also, although the example illustrated in FIG. 1 illustrates a situation of surgery as an example of a medical procedure, the medical procedure in which the surgical video microscope device 510 is used is not limited to surgery, and may be any of various other types of medical procedures such as an examination using an endoscope.

Beside the operating table 530, the surgical video microscope device 510 according to the present embodiment is provided. The surgical video microscope device 510 is equipped with a base section 511 which acts as a base, an arm section 512 which extends from the base section 511, and an imaging unit 515 connected as a front edge unit on the front edge of the arm section 512. The arm section 512 includes multiple joint sections 513a, 513b, and 513c, multiple links 514a and 514b joined by the joint sections 513a and 513b, and the imaging unit 515 provided on the front edge of the arm section 512. In the example illustrated in FIG. 1, for the sake of simplicity, the arm section 512 includes three joint sections 513a to 513c and two links 514a and 514b, but in actuality, the degrees of freedom in the positions and the attitudes of the arm section 512 and the imaging unit 515 may be considered to appropriately configure factors such as the numbers and shapes of the joint sections 513a to 513c and the links 514a and 514b, and the directions of the drive shafts of the joint sections 513a to 513c, so as to achieve the desired degrees of freedom.

The joint sections 513a to 513c have a function of rotatably joining the links 514a and 514b to each other, and by driving the rotation of the joint sections 513a to 513c, the driving of the arm section 512 is controlled. Herein, in the following description, the position of each structural member of the surgical video microscope device 510 means the position (coordinates) in a space prescribed for drive control, while the attitude of each structural member means the direction (angle) with respect to an arbitrary axis in the space prescribed for drive control. Also, in the following description, the driving (or the drive control) of the arm section 512 refers to either or both of the driving (or the drive control) of the joint sections 513a to 513c, and the change (or change being controlled) of the position and attitude of each structural member of the arm section 512 by conducting the driving (or the drive control) of the joint sections 513a to 513c.

On the front edge of the arm section 512, the imaging unit 515 is connected as a front edge unit. The imaging unit 515 is a unit that acquires an image of an imaging target, and is a device such as a camera capable of capturing a moving image or a still image, for example. As illustrated in FIG. 1, the attitudes and the positions of the arm section 512 and the imaging unit 515 are controlled by the surgical video microscope device 510 so that the imaging unit 515 provided on the front edge of the arm section 512 captures the operating site of the subject 540. Note that the configuration of the imaging unit 515 connected as the front edge unit on the front edge of the arm section 512 is not particularly limited, and the imaging unit 515 may be configured as an endoscope or a microscope, for example. Additionally, the imaging unit 515 may also be configured to be attachable to and removable from the arm section 512. According to such a configuration, an imaging unit 515 depending on the usage scenario may be connected appropriately to the front edge of the arm section 512 as the front edge unit, for example. Note that although the description herein focuses on a case in which the imaging unit 515 is applied as the front edge unit, obviously the front edge unit connected to the front edge of the arm section 512 is not necessarily limited to the imaging unit 515.

Also, at a position facing the user 520, a display device 550 such as a monitor or a display is installed. An image of the operating site captured by the imaging unit 515 is displayed as an electronic image on the display screen of the display device 550. The user 520 performs various treatments while looking at an electronic image of the operating site displayed on the display screen of the display device 550.

In this way, in the medical field, the present embodiment proposes performing surgery while imaging the operating site with the surgical video microscope device 510.

Particularly, the surgical video microscope device 510 according to an embodiment of the present disclosure (that is, a medical observation device) is configured to be able to acquire image data for displaying the imaging target as a three-dimensional image (3D image).

As a specific example, the surgical video microscope device 510 is provided with a stereo camera including two imaging section subsystems (for example, camera units) as the imaging unit 515, and thereby acquires, via each imaging section, images from multiple different viewpoints (in other words, viewpoint images).

Each of the multiple viewpoint images acquired by the imaging unit 515 is subjected to various types of image processing by an image processing device built into or externally attached to the surgical video microscope device 510, and then displayed on the display device 550 as a right-eye image and a left-eye image, respectively. Note that in this description, the right-eye image denotes a so-called parallax image having a set parallax for observing a viewpoint corresponding to the user's right eye, to enable the user to observe a 3D image. Similarly, the left-eye image denotes a parallax image having a set parallax for observing a viewpoint corresponding to the user's left eye, to enable the user to observe a 3D image.

Note that a variety of techniques have been proposed as a mechanism for enabling the user 520 to observe, as a 3D image, the images displayed on the display device 550 as the right-eye image and the left-eye image. As a specific example, there is a technique in which special-purpose eyeglasses are used to cause the left and right eyes to observe mutually different images (in other words, a right-eye image and a left-eye image). Also, in recent years, glasses-free 3D picture technology which enables the observation of a three-dimensional image without the use of special-purpose eyeglasses has also been proposed.

In addition, the circumstances in which a medical observation device as described above is used also include cases in which various information should be checked, including images of an affected area. Under such circumstances, usage patterns such as displaying images respectively on multiple displays or displaying multiple images inside a display may also be anticipated. As a specific example, a case is anticipated in which an overall picture of the affected area is displayed on one display, while a magnified image of the affected area is displayed on another display. As another example, a case is also anticipated in which an image of the affected area is displayed on one display, while an image captured by another imaging device, such as a computed tomography (CT) image or a magnetic resonance imaging (MRI) image, is displayed on another display. For this reason, multiple display devices 550 may also be provided in some cases.

The above thus references FIG. 1 to describe, as an applied example of using a medical observation device according to the present embodiment, an example of a case in which a surgical video microscope device equipped with an arm is used as the medical observation device.

<1-2. Exterior Appearance of Medical Observation Device>

Figure 2:
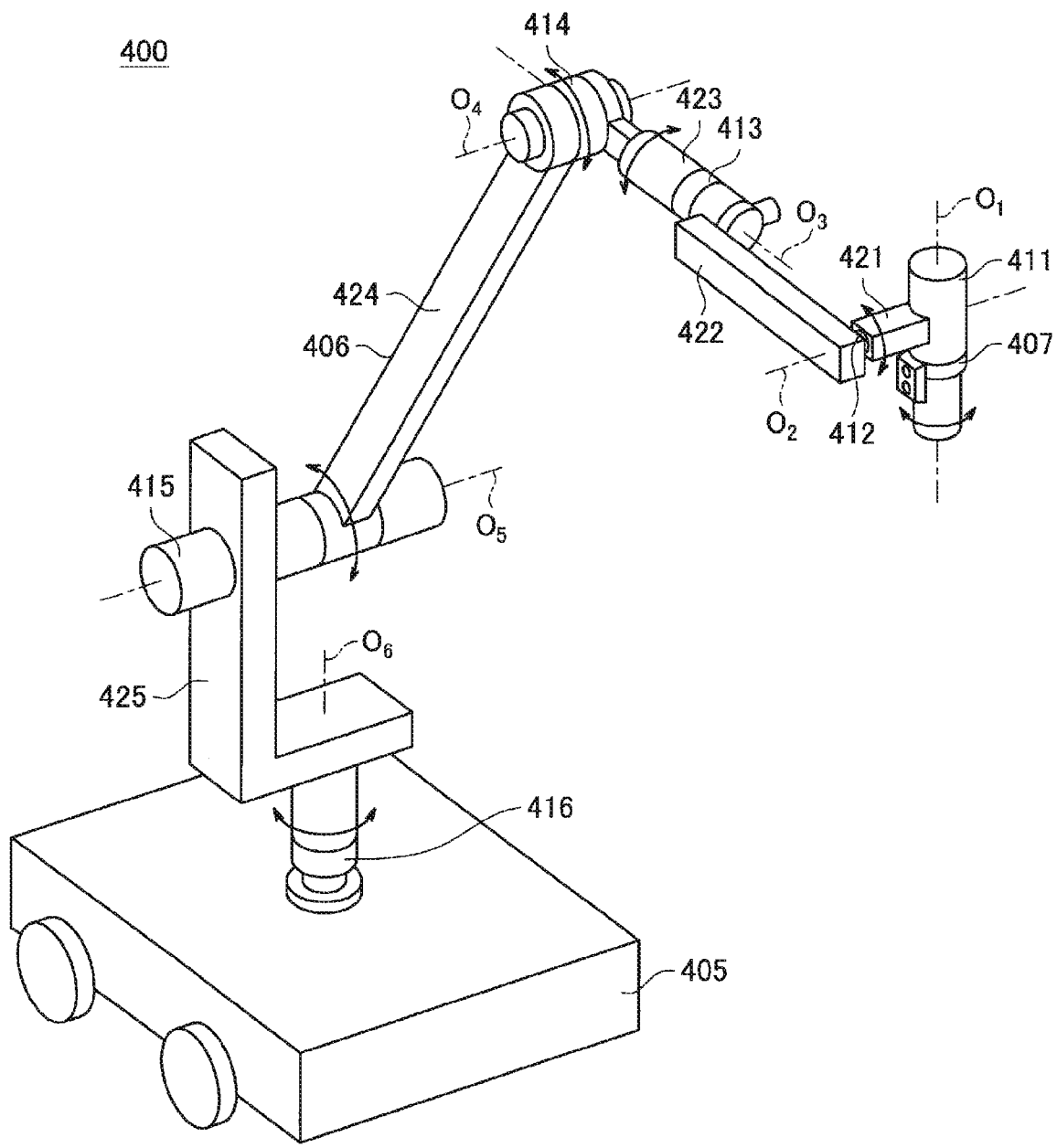
FIG. 2 is a schematic diagram illustrating one example of the exterior appearance of a medical observation device according to one embodiment of the present disclosure.

Next, FIG. 2 will be referenced to describe a schematic configuration of a surgical video microscope device provided with an arm as an example of a surgical video microscope device (that is, a medical observation device) that acquires image data (that is, viewpoint images imaged from multiple viewpoints) for displaying an imaging target as a three-dimensional image, in a medical observation system according to an embodiment of the present disclosure. FIG. 2 is a schematic diagram illustrating an example of the exterior appearance of a medical observation device according to an embodiment of the present disclosure.

As illustrated in FIG. 2, an observation device 400 serving as an example of a medical observation device according to the present embodiment includes a base section 405, a support section 406, and an imaging unit 407. For example, the base section 405 is configured to be movable on a floor surface, and supports the support section 406. In addition, the imaging unit 407 is supported at the front edge of the support section 406.

The imaging unit 407 is a unit that acquires an image of an imaging target, and may include a device such as a camera that captures a moving image or a still image, for example. The imaging unit 407 is configured as a microscope section, for example. Further, by controlling the driving of the support section 406, the position and attitude of the imaging unit 407 are controlled. In the present embodiment, the imaging unit 407 images a partial region of a patient's body, the partial region being an operating site, for example. Note that, as described above, in the observation device 400 according to the present embodiment, the imaging unit 407 is configured to be able to acquire images from multiple different viewpoints (that is, image data for displaying the imaging target as a three-dimensional image), like a stereo camera, for example.

For example, the support section 406 includes joint sections 411 to 416 and arm sections 421 to 425. For example, in the example illustrated in FIG. 2, four sets each including two arm sections, and a joint section that rotatably joints one (front edge side) of the two arm sections to the other one (rear edge side) are included.

The joint section 411 rotatably holds the imaging unit 407 on the front edge side, and is held by the arm section 421 on the rear edge side in a state of being fixed to the front edge section of the arm section 421. The joint section 411 has a cylindrical shape, and holds the imaging unit 407 so as to be rotatable around a first axis $O_1$ being a central axis in a height direction. The arm section 421 has a shape extending from the side surface of the joint section 411 in a direction orthogonal to the first axis $O_1$.

The joint section 412 rotatably holds the arm section 421 on the front edge side, and is held by the arm section 422 on the rear edge side in a state of being fixed to the front edge section of the arm section 422. The joint section 412 has a cylindrical shape, and holds the arm section 421 so as to be rotatable around a second axis $O_2$ being a central axis in the height direction, and an axis orthogonal to the first axis $O_1$. The arm section 422 has a substantially L-shape, and is joined to the joint section 412 at an edge section of a vertical line portion of the L-shape.

The joint section 413 rotatably holds a horizontal line portion of the L-shape of the arm section 422 on the front edge side, and is held by the arm section 423 on the rear edge side in a state of being fixed to the front edge section of the arm section 423. The joint section 413 has a cylindrical shape, and holds the arm section 422 so as to be rotatable around a third axis $O_3$ being a central axis in the height direction, an axis orthogonal to the second axis $O_2$, and an axis parallel to a direction in which the arm section 422 extends. The front edge side of the arm section 423 has a cylindrical shape, and a hole section penetrating through in a direction orthogonal to the height direction of the cylinder of the front edge side is formed on the rear edge side. The joint section 413 is rotatably held by the joint section 414 via the hole section.

The joint section 414 rotatably holds the arm section 423 on the front edge side, and is held by the arm section 424 on the rear edge side in a state of being fixed to the arm section 424. The joint section 414 has a cylindrical shape, and holds the arm section 423 so as to be rotatable around a fourth axis $O_4$ being a central axis in the height direction, and an axis orthogonal to the third axis $O_3$.

The joint section 415 rotatably holds the arm section 424 on the front edge side, and is fixedly attached to the arm section 425 on the rear edge side. The joint section 415 has a cylindrical shape, and holds the arm section 424 so as to be rotatable around a fifth axis $O_5$ being a central axis in the height direction, and an axis parallel to the fourth axis $O_4$. The arm section 425 includes a portion having an L-shape, and a rod-shaped portion extending downward from a horizontal line portion of the L-shape. The joint section 415 is attached to an edge section of a vertical line portion of the L-shape of the arm section 425 on the rear edge side.

The joint section 416 rotatably holds the arm section 425 on the front edge side, and is fixedly attached to the top surface of the base section 405 on the rear edge side. The joint section 416 has a cylindrical shape, and holds the arm section 425 so as to be rotatable around a sixth axis $O_6$ being a central axis in the height direction, and an axis orthogonal to the fifth axis $O_5$. A rear edge section of the rod-shaped portion of the arm section 425 is attached to the front edge side of the joint section 416.

The support section 406 having the configuration described above realizes motions with six degrees of freedom in total having three translational degrees of freedom and three rotational degrees of freedom in the imaging unit 407 (microscope section).

<1-3. Investigation of Medical Observation Device>

In a stereoscopic observation device that causes an image of a subject (observation target) to be observed as a stereoscopic 3D image, as described above, for example, images of the subject from multiple different viewpoints (that is, viewpoint images) are acquired by an imaging unit (what is called a stereo camera) including multiple image sensors (imaging units). Additionally, the viewpoint images captured by each of the image sensors are controlled to be observed by different eyes among the left eye and the right eye of the user. According to such a configuration, the user becomes able to observe the images of the subject as a stereoscopic 3D image.

Such a stereoscopic observation device is achievable by providing an imaging optical system that includes for example an objective optical system and two image-forming optical systems for the right eye and the left eye, which have a different optical axis than the optical axis of the objective optical system and which cause light condensed by the objective optical system to form an image. Also, the above imaging optical system may include a focus lens (one example of a focusing optical member) for focusing the objective optical system, such that the focal length (or magnification) by the image-forming optical systems is changeable.

According to such a configuration, since focus is not lost even if a zoom operation that changes the focal length (or magnification) by the image-forming optical systems is performed, there is the merit of not having to move the focus lens in association with a zoom operation. Note that in the following, the focal length by the image-forming optical systems or the magnification by the image-forming optical systems will be called information related to a zoom operation in some cases.

On the other hand, in the imaging optical system described above, in some cases an image movement phenomenon occurs in which the subject image obtained by imaging moves in association with the movement of the focus lens included in the objective optical system even though the subject is not moving.

Figure 3:
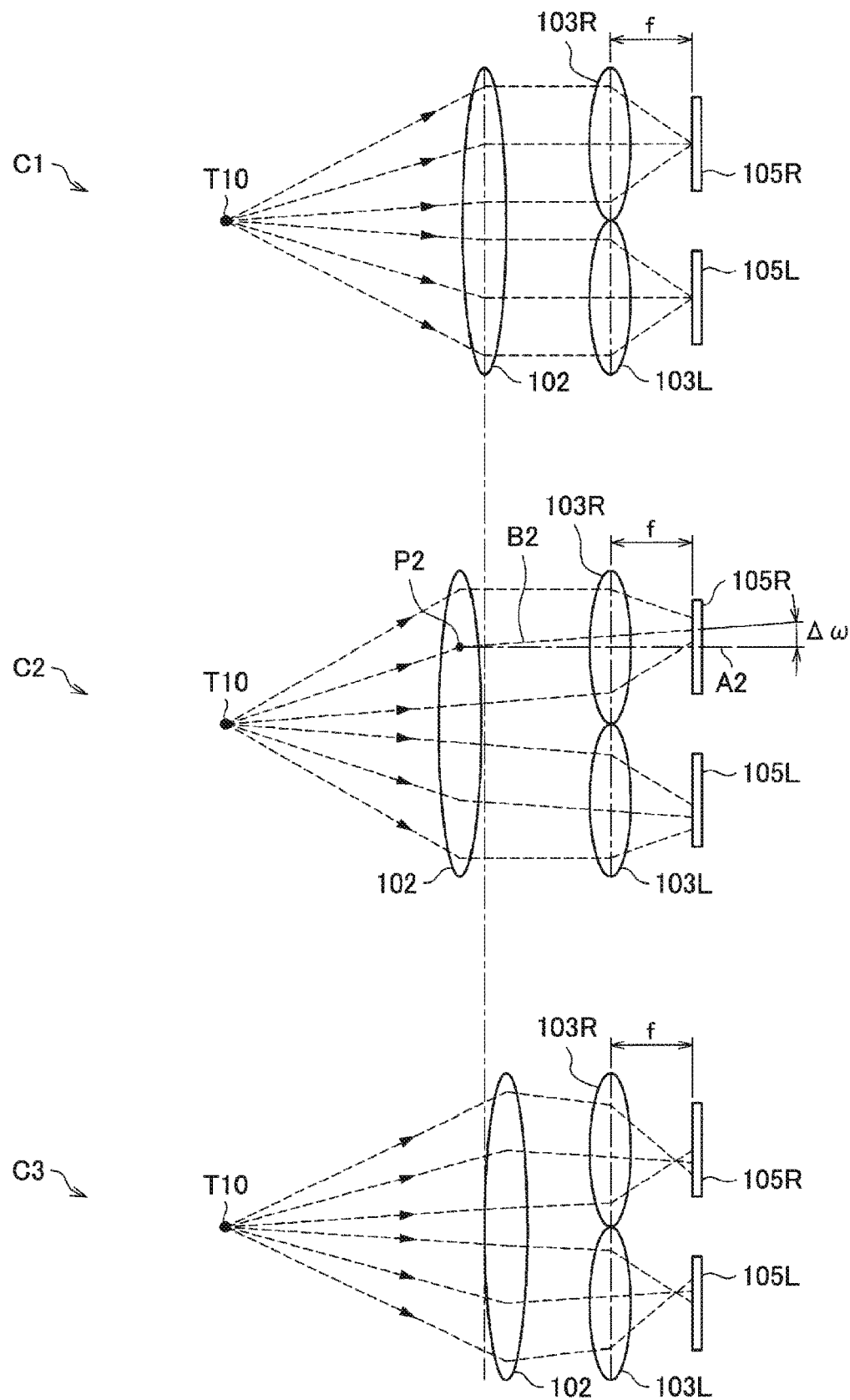
FIG. 3 is an explanatory diagram for explaining an image movement phenomenon.
Figure 4:
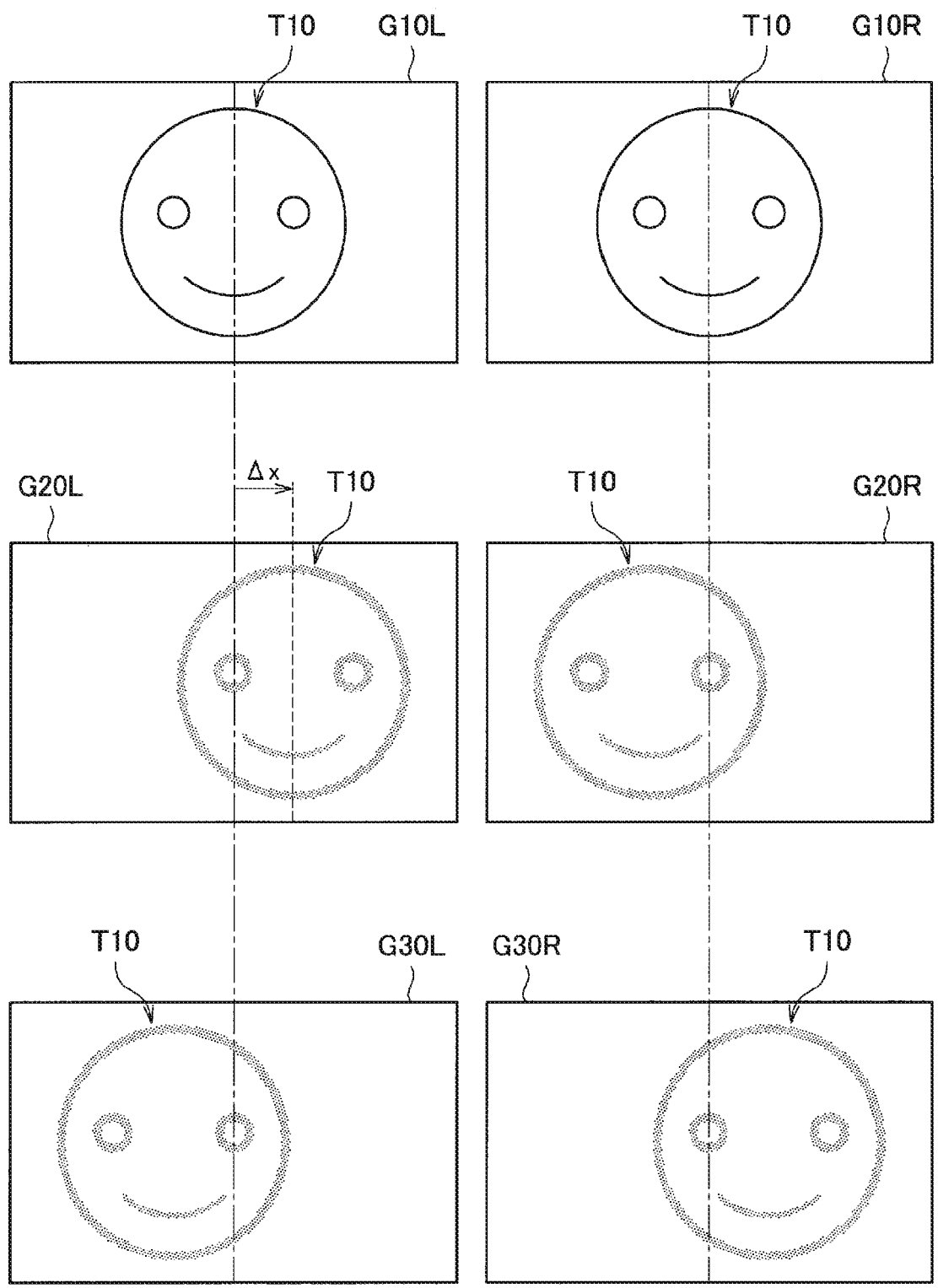
FIG. 4 is an explanatory diagram for explaining an image movement phenomenon.

FIGS. 3 and 4 are explanatory diagrams for explaining the image movement phenomenon. In FIG. 3, a focus lens 102 is illustrated as one example of the objective optical system, a zoom lens 103L is illustrated as one example of an image-forming optical system for the left eye, and a zoom lens 103R is illustrated as one example of an image-forming optical system for the right eye. Also, in FIG. 3, an image sensor 105L for the left eye and an image sensor 105R for the right eye are illustrated.

As illustrated in FIG. 3, light from the subject T10 is condensed by the focus lens 102 and incident on the zoom lens 103L and the zoom lens 103R. Also, the light condensed by the focus lens 102 is formed into an image on the photosensitive face of the image sensor 105L by the zoom lens 103L, or formed into an image on the photosensitive face of the image sensor 105R by the zoom lens 103R. Note that the state C1 illustrated in FIG. 3 is a state in which the subject T10 is in focus. Also, the state C2 is a state in which the focal point is shifted far (more distant) compared to the state C1, and the state C3 is a state in which the focal point is shifted near (closer) compared to the state C1.

In the state C1, as illustrated in FIG. 4, in a left-eye image G10L obtained by the image sensor 105L and a right-eye image G10R obtained by the image sensor 105R, the image of the subject T10 appears in the center.

On the other hand, in the state C2, in a left-eye image G20L obtained by the image sensor 105L and a right-eye image G20R obtained by the image sensor 105R, the image of the subject T10 is in a blurry state and has moved to the right and to the left, respectively.

Also, in the state C3, in a left-eye image G30L obtained by the image sensor 105L and a right-eye image G30R obtained by the image sensor 105R, the image of the subject T10 is in a blurry state and has moved to the left and to the right, respectively.

Herein, the image movement amount Δx from the left-eye image G10L in the state C1 to the left-eye image G20L in the state C2 is obtained by the following Formula (1) using the focal length f and the angle Δω of the zoom lens 103R illustrated in FIG. 3 and the pixel pitch d of the image sensor 105L.

$$\Delta x = f \times \tan \Delta\omega \div d \tag{1}$$

Note that in the state C2 illustrated in FIG. 3, the angle Δω denotes the angle obtained between an optical axis A2 of the zoom lens 103R and an optical axis B2 that passes through an intersection point P2 between the focus lens 102 and the optical axis A2 and is incident on the zoom lens 103R.

Figure 5:
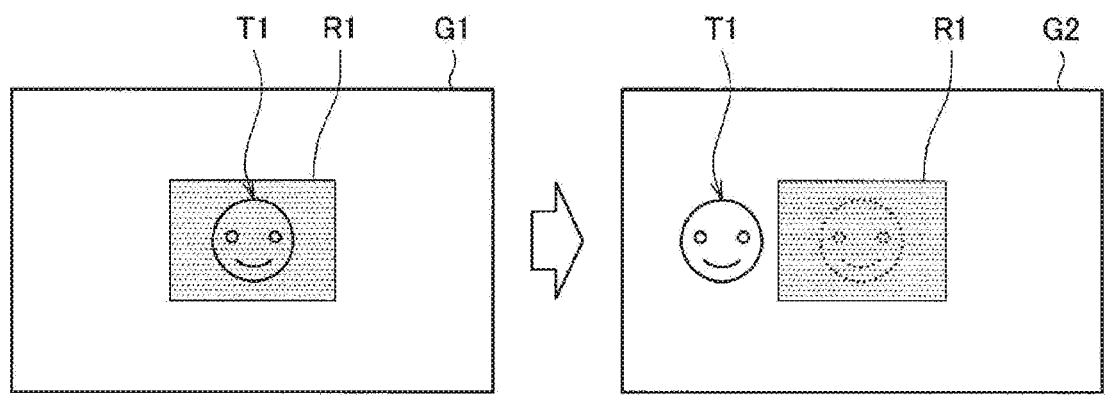
FIG. 5 is an explanatory diagram for explaining image movement during an AF operation.

Next, realizing an autofocus (AF) function that automatically focuses by moving the focus lens in an observation device provided with an imaging optical system in which the image movement phenomenon occurs as above will be considered. When the focus lens moves in association with the autofocus (AF) operation, the image movement phenomenon may occur. For example, since an AF operation is executed to move the focus lens to align the focal point with (bring into focus) a predetermined target region (hereinafter called the AF ranging region in some cases), if the image movement phenomenon occurs, there is a risk of the AF operation not functioning correctly. FIG. 5 is an explanatory diagram for explaining image movement during an AF operation.

In the image G1 (for example, a left-eye image) illustrated in FIG. 5, the AF ranging region R1 is disposed in the screen center, and the subject T1 is included in the AF ranging region R1. At this point, if an AF operation is started, the focus lens moves to bring into focus the subject T1 included in the AF ranging region R1, and the subject T1 in the image (subject image) moves. As a result, if the subject T1 is no longer included in the AF ranging region R1 in the screen center like the image G2 illustrated in FIG. 5, there is a risk of being unable to bring the subject T1 into focus (the AF operation not functioning correctly).

Also, as illustrated in Formula (1) above, since the amount of movement of the subject image (image movement amount) is a magnitude depending on the focal length f of the image-forming optical system, in an observation device capable of observing at longer focal lengths, bringing the subject into focus may become more difficult. For example, observation devices that include a zoom function are capable of observing at long focal lengths in many cases.

Figure 6:
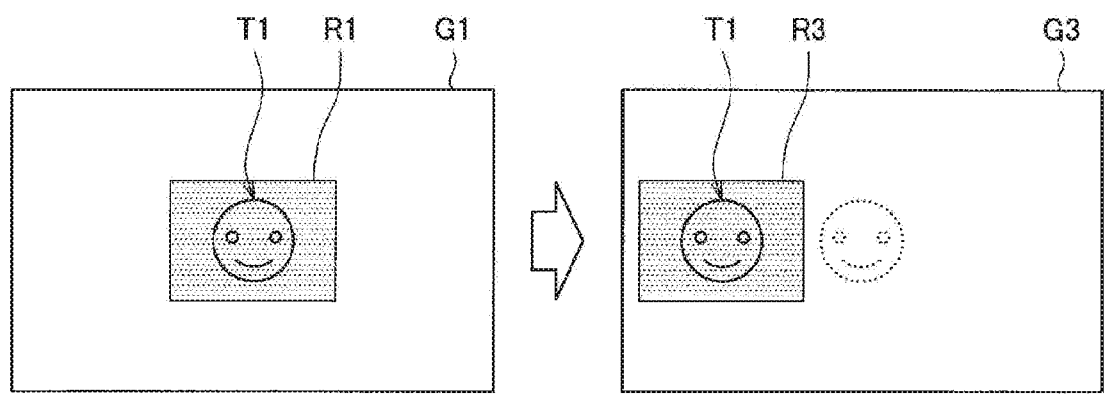
FIG. 6 is an explanatory diagram for explaining an overview of the present embodiment.

Accordingly, focusing on the above circumstances led to the creation of one embodiment of the present disclosure. According to the present embodiment, it is possible to bring the subject into focus, even in the case in which the subject image moves in association with an AF operation. FIG. 6 is an explanatory diagram for explaining an overview of the present embodiment.

The image G1 illustrated in FIG. 6 is similar to the image G1 illustrated in FIG. 5. Here, if an AF operation is started, the subject T1 in the image moves, but in the present embodiment, the AF ranging region moves in association with the movement of the subject T1 in the image. As a result, since the subject T1 in the image is included in the AF ranging region R3 like the image G3 illustrated in FIG. 6, it becomes possible to bring the subject T1 into focus by continuing the AF operation. Hereinafter, in one embodiment of the present disclosure, an exemplary configuration for realizing the above advantageous effect will be described.

2. Configuration

Figure 7:
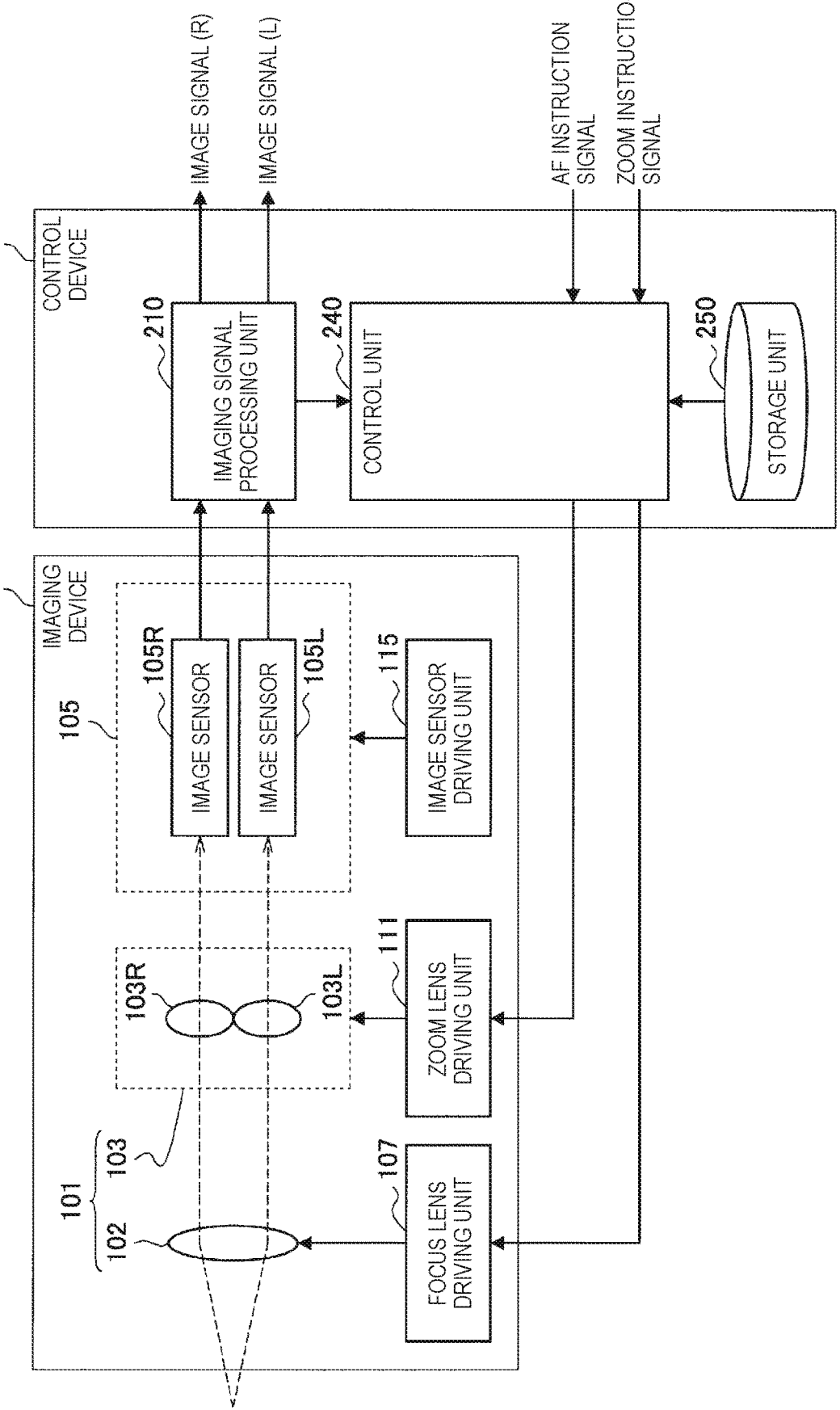
FIG. 7 is a block diagram illustrating one example of a functional configuration of the medical observation device according to one embodiment of the present disclosure.

First, FIG. 7 describes one example of a functional configuration of the medical observation device according to one embodiment of the present disclosure. FIG. 7 is a block diagram illustrating one example of a functional configuration of the medical observation device according to one embodiment of the present disclosure.

As illustrated in FIG. 7, the medical observation device 1 according to the present embodiment is provided with an imaging device 10 and a control device 20 that executes various control processes and signal processing related to operations of the imaging device 10. Note that the example illustrated in FIG. 7 illustrates an example in which the imaging device 10 and the control device 20 are included in a single housing.

Hereinafter, the configuration of the imaging device 10 and the control device 20 will be described in further detail. First, the configuration of the imaging device 10 will be described.

The imaging device 10 includes an imaging optical system 101, an image sensor 105R, and an image sensor 105L. Note that in this description, for the sake of convenience, the image sensor 105R is described as capturing a right-eye image and the image sensor 105L is described as capturing a left-eye image, but the image sensor 105R and the image sensor 105L are collectively called the image sensor 105 in some cases.

Also, the imaging device 10 includes a focus lens driving unit 107, a zoom lens driving unit 111, and an image sensor driving unit 115 as functions thereof.

The imaging optical system 101 includes a focus lens 102 that is a focusing optical member, as well as a zoom lens 103R and a zoom lens 103L that are zooming optical members. Note that in the following, the zoom lens 103R and the zoom lens 103L will be collectively called the zoom lens 103 in some cases.

Also, in FIG. 7, only the focus lens 102 and the zoom lens 103 are illustrated representatively, but the imaging optical system 101 may also include various types of optical members, such as other lenses and filters.

The focus lens 102 may also be a part of the objective optical system included in the imaging optical system 101. Additionally, the zoom lens 103R and the zoom lens 103L may also be a part of each of the two image-forming optical systems (the image-forming optical system for the right eye and the image-forming optical system for the left eye) included in the imaging optical system 101. In other words, as illustrated in FIG. 7, the zoom lens 103R and the zoom lens 103L cause light condensed by the focus lens 102 to form an image on the photosensitive face of the image sensor 105R and the image sensor 105L, respectively.

The focus lens 102 is a lens for adjusting the focal length of the imaging optical system 101. The focus lens 102 is configured to be movable on the optical axis, and by controlling the position on the optical axis of the focus lens 102, the focusing distance of the imaging optical system 101 is adjusted. Note that the focus lens 102 is one example of an adjustment optical member for adjusting the focusing distance of the imaging optical system 101. By having the focus lens 102 move, the focusing distance for the left eye and the focusing distance for the right eye may be adjusted at the same time.

The zoom lens 103 is a lens for adjusting the magnification of the imaging optical system 101. The zoom lens 103 is configured to be movable on the optical axis, and by controlling the position on the optical axis of the zoom lens 103, the magnification of the imaging optical system 101 is adjusted. Note that, as illustrated in FIG. 7, the optical axes of the zoom lens 103R and the zoom lens 103L are different from each other.

Also, the zoom lens zoom lens 103 is an example of an optical member for adjusting the magnification of the imaging optical system 101. In the present embodiment, it is sufficient to adjust the magnification of the imaging optical system 101 by adjusting the position on the optical axis of at least one optical member included in each image-forming optical system, and the number and type of optical members configured to be movable to adjust the magnification are not limited.

The image sensor 105 (image sensor 105R and image sensor 105L) takes an image of a subject by receiving observation light on its photosensitive face. Specifically, the image sensor 105 includes a photosensitive face on which photosensors such as photodiodes are arrayed, and by receiving observation light on the photosensitive face, acquires by photoelectric conversion an imaging signal, which is an electrical signal corresponding to the observation light, or in other words an electrical signal corresponding to a subject image. The configuration of the image sensor 105 is not limited, and any of various known types of image sensors may be used as the image sensor 105, such as a charge-coupled device (CCD) image sensor or a complementary metal-oxide-semiconductor (CMOS) image sensor for example. The imaging signal acquired by the image sensor 105 is transmitted to an imaging signal processing unit 210 of the control device 20 described later.

The focus lens driving unit 107 includes a motor and a driver circuit that supplies a driving current to the motor, for example, and moves the focus lens 102 along the optical axis. The operations of the focus lens driving unit 107 are controlled by a focus lens driving control unit not illustrated. The focus lens driving control unit includes any of various types of processors such as a CPU or a DSP, or a microcontroller or the like, and controls the operations of the focus lens driving unit 107. The focus lens driving control unit may also include any of various types of integrated circuits, such as an FPGA, a driver IC, and/or a dedicated LSI chip (that is, an ASIC). The functions of the focus lens driving control unit may be realized by having a processor included in the focus lens driving control unit execute computational processing in accordance with a predetermined program.

Specifically, the medical observation device 1 includes an autofocus (AF) function. By having the focus lens driving control unit control the driving of the focus lens driving unit 107 in accordance with a movement amount of the focus lens 102 computed according to a predetermined AF method by a control unit 240 of the control device 20 described later, the focus lens 102 moves by an amount equal to the movement amount, and the focusing distance of the imaging optical system 101 is adjusted.

The zoom lens driving unit 111 includes a motor and a driver circuit that supplies a driving current to the motor, for example, and moves the zoom lens 103 along the optical axis. The operations of the zoom lens driving unit 111 are controlled by a zoom lens driving control unit not illustrated. The zoom lens driving control unit includes any of various types of processors, such as a central processing unit (CPU) or a digital signal processor (DSP), or a microcontroller or the like on which a processor is mounted together with a storage element such as memory, and controls the operations of the zoom lens driving unit 111. The zoom lens driving control unit may also include any of various types of integrated circuits, such as a field-programmable gate array (FPGA), a driver integrated circuit (IC), and/or a dedicated large-scale integration (LSI) chip (that is, an application-specific integrated circuit (ASIC)). The functions of the zoom lens driving control unit may be realized by having a processor included in the zoom lens driving control unit execute computational processing in accordance with a predetermined program.

Specifically, by having the zoom lens driving control unit control the driving of the zoom lens driving unit 111 in accordance with a movement amount of the zoom lens 103 computed by the control unit 240 of the control device 20 described later, the zoom lens 103 moves by an amount equal to the movement amount, and the magnification of the imaging optical system 101 is adjusted. Note that in the case in which another optical member besides the zoom lens 103 is also configured to be movable to adjust the magnification of the imaging optical system 101, the other optical member may also be moved on the optical axis by the zoom lens driving unit 111 according to control from the zoom lens driving control unit.

The image sensor driving unit 115 corresponds to a driver for driving the image sensor 105. The image sensor driving unit 115 supplies a driving signal (a signal for driving the transistors and the like mounted in the image sensor 105) to the image sensor 105 at predetermined timings, thereby causing the image sensor 105 to execute operations such as image-taking operations and reset operations at predetermined timings, and to acquire an imaging signal corresponding to a subject image. Note that, although omitted from illustration, an image sensor driving control unit that controls the operations of the image sensor driving unit 115 may be provided in the imaging device 10 or the control device 20. The image sensor driving control unit includes any of various types of processors, such as a CPU or a DSP, or a microcontroller or the like, and by indicating to the image sensor driving unit 115 the timings at which to supply the above driving signal to the image sensor 105, controls the driving of the image sensor 105 through the image sensor driving unit 115. Note that the functions of the image sensor driving control unit may be realized by having a processor included in the image sensor driving control unit execute computational processing in accordance with a predetermined program.

In the medical observation device 1, the starting and ending of image-taking may be controlled according to an instruction by a surgeon through an input device (not illustrated) such as a switch. Specifically, the medical observation device 1 is provided with an input device for inputting an instruction signal to start taking an image, and by having the above image sensor driving control unit control the driving of the image sensor 105 in accordance with the instruction by the surgeon through the input device, the starting and ending of image-taking may be executed.

Note that the configurations corresponding to the zoom lens driving control unit, the focus lens driving control unit, and/or the image sensor driving control unit described above may be mounted in the imaging device 10 or in the control device 20.

The above describes the configuration of the imaging device 10. Next, the configuration of the control device 20 will be described. The control device 20 includes an imaging signal processing unit 210, a control unit 240, and a storage unit 250 as functions thereof.

The control device 20 includes any of various types of processors and a storage element such as memory, for example. Each function of the control device 20 above is realized by having a processor included in the control device 20 execute computational processing in accordance with a predetermined program.

The imaging signal processing unit 210 executes any of various types of signal processing for displaying a subject image on a display device (not illustrated), such as a gamma correction process and a white balance adjustment process, on the imaging signal acquired by the image sensor 105. A right-eye imaging signal and a left-eye imaging signal (hereinafter designated the image signal (R) and the image signal (L)) having been subjected to the various signal processing by the imaging signal processing unit 210 are transmitted to a display device, and on the display device, a stereoscopic 3D image of the subject appears on the basis of the image signal (R) and the image signal (L). In addition, the imaging signal processing unit 210 also provides the image signal (R) and the image signal (L) to the control unit 240. Note that in the following description, the image signal (R) and the image signal (L) will also be designated simply the image signal in some cases.

Figure 8:
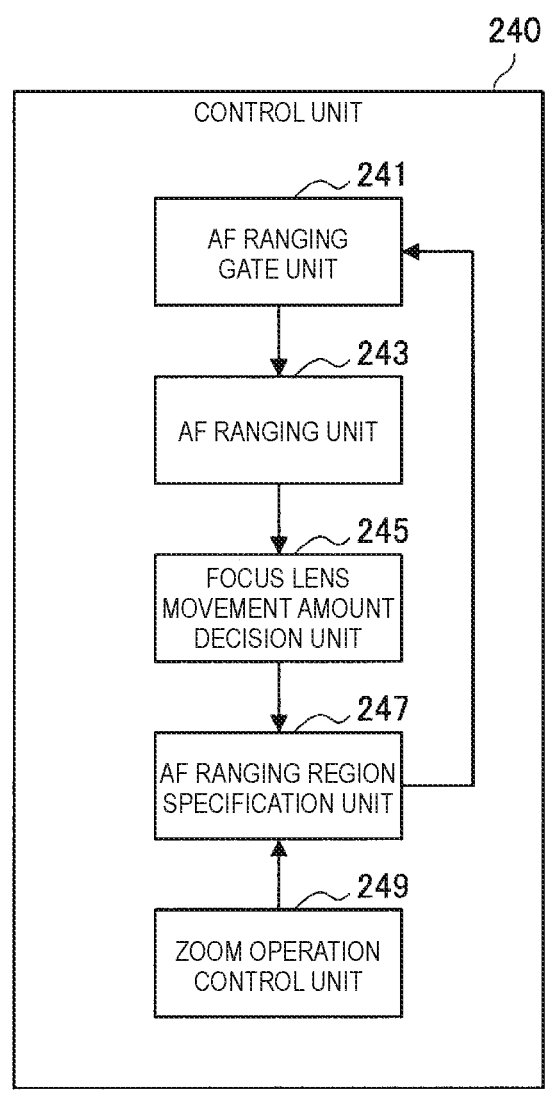
FIG. 8 is a block diagram illustrating one example of a functional configuration of a control unit 240.

The control unit 240 executes various types of controls related to the AF operations and the zoom operations of the imaging device 10. The functions of the control unit 240 will be described in detail with reference to FIG. 8. FIG. 8 is a block diagram illustrating one example of a functional configuration of the control unit 240. As illustrated in FIG. 8, the control unit 240 functions as an AF ranging gate unit 241, an AF ranging unit 243, a focus lens movement amount decision unit 245, an AF ranging region specification unit 247, and a zoom operation control unit 249.

The AF ranging gate unit 241, the AF ranging unit 243, the focus lens movement amount decision unit 245, and the AF ranging region specification unit 247 are functions for controlling AF operations. The control unit 240 executes a series of processes related to AF operations in accordance with an instruction signal (AF instruction signal) for executing an AF operation input by the user (for example, the surgeon). The AF instruction signal may be input via any of various types of input devices not illustrated which is provided on the medical observation device 1, such as a switch, for example.

The AF method executed by the control unit 240 is not limited, but the following describes an example in which the AF method executed by the control unit 240 is the contrast method. The contrast method is a method of performing a focusing operation by moving a focusing optical member (in the illustrated example, the focus lens 102) included in the imaging optical system 101 while also searching for a position of the optical member at which the contrast in the subject image is maximized, and causing the optical member to move to the position where the contrast is maximized.

The AF ranging gate unit 241 extracts the image data of the AF ranging region on the basis of the image signal obtained by the imaging signal processing unit 210 and the AF ranging region specified by the AF ranging region specification unit 247, and provides the image data to the AF ranging unit 243. Note that the AF ranging gate unit 241 may also extract the image data of the AF ranging region from either one of the image signal (R) and the image signal (L), and provide the image data to the AF ranging unit 243.

The AF ranging unit 243 specifies an AF evaluation value indicating the degree of focusing of the imaging optical system 101 on the basis of the image data of the AF ranging region. For example, the AF ranging unit 243 extracts the contrast from the image data of the AF ranging region, and provides information about the contrast to the focus lens movement amount decision unit 245.

The focus lens movement amount decision unit 245 decides the movement amount of the focus lens 102 on the basis of the information about the contrast detected by the AF ranging unit 243. Specifically, the focus lens movement amount decision unit 245 decides the movement amount of the focus lens 102 on the basis of the contrast in the previous step and the contrast in the current step, such that the focus lens 102 moves on the optical axis by a predetermined distance in the direction of increasing contrast. Note that in the initial step (in the case in which information about the contrast from a previous step does not exist), it is sufficient to decide the movement amount of the focus lens 102 such that the focus lens 102 is moved by a predetermined distance in a predetermined direction set in advance.

Information about the decided movement amount of the focus lens 102 is transmitted to the focus lens driving control unit not illustrated. The focus lens 102 is made to move by the decided movement amount by the focus lens driving control unit through the focus lens driving unit 107.

The AF ranging region specification unit 247 specifies the AF ranging region for AF operations on the basis of the position or the movement amount of the focus lens 102. For example, the AF ranging region specification unit 247 may specify the image movement direction and the image movement amount of the subject image associated with an AF operation described with reference to FIGS. 3 to 6 on the basis of a cumulative movement value since the start of the AF operation (one example of the movement amount), and specify the AF ranging region on the basis of the image movement direction and the image movement amount.

Also, the AF ranging region specification unit 247 may specify the image movement direction and the image movement amount on the additional basis of information related to a zoom operation provided by the zoom operation control unit 249. As in Formula (1) described with reference to FIGS. 3 and 4, the image movement amount may be specified on the basis of the focal length of the zoom lens 103R (one example of information related to the zoom operation).

For example, the AF ranging region specification unit 247 may specify the movement amount on the basis of a data table associating information related to the zoom operation with the image movement direction and the image movement amount in the case of moving the focus lens 102 in a predetermined direction by a predetermined amount (for example, the minimum unit of movement for the focus lens 102). In such a case, the above data table may also be stored in the storage unit 250 described later, for example.

Additionally, the AF ranging region specification unit 247 may also compute the image movement direction and the image movement amount using Formula (1) for example. In such a case, information related to the correspondence between the angle $\Delta\omega$ in Formula (1) and the position of the focus lens as well as information related to the pixel pitch d of the image sensor 105 may also be stored in the storage unit 250 described later, for example.

On the basis of the image movement direction and the image movement amount, the AF ranging region specification unit 247 may also specify a region obtained by moving from the AF ranging region at the start time of the AF operation by the image movement amount as the AF ranging region, and provide information related to the specification of the AF ranging region to the AF ranging gate unit 241.

Note that the image movement amount, the image movement direction, and the AF ranging region may be specified for each of the image signal (R) and the image signal (L), or may be specified only for one image signal set as a target of extraction by the AF ranging gate unit 241.

Also, in the case in which the size of the AF ranging region is predetermined, the AF ranging region specification unit 247 may specify a position related to the AF ranging region, and provide information about the position related to the AF ranging region to the AF ranging gate unit 241.

The zoom operation control unit 249 executes various types of controls related to the zoom operations of the medical observation device 1. Specifically, an instruction signal (zoom instruction signal) for executing a zoom operation may be input into the medical observation device 1 by the user (for example, the surgeon). The zoom instruction signal is input via any of various types of input devices not illustrated which is provided on the medical observation device 1, such as a switch, for example. The zoom instruction signal also includes an instruction regarding magnification for example, and the zoom operation control unit 249 decides a movement amount of the zoom lens 103 that may achieve the indicated magnification on the basis of the zoom instruction signal. Information about the decided movement amount is transmitted to the zoom lens driving control unit not illustrated. The zoom lens 103 is made to move by the decided movement amount by the zoom lens driving control unit through the zoom lens driving unit 111, thereby causing the magnification of the imaging optical system 101 to be adjusted in accordance with the user instruction. Note that in the case in which another optical member besides the zoom lens 103 is also configured to be movable to adjust the magnification of the imaging optical system 101, the zoom operation control unit 127 may also decide a movement amount on the optical axis for the other optical member as well.

Also, the zoom operation control unit 249 provides information related to the zoom operation based on the zoom instruction signal (for example, the magnification after the zoom operation or the focal length of the zoom lens 103) to the AF ranging region specification unit 247.

Note that the storage unit 250 illustrated in FIG. 7 stores programs and parameters by which each configuration unit of the control device 20 functions. For example, the storage unit 250 may store the data table described above.

3. Operations

Figure 9:
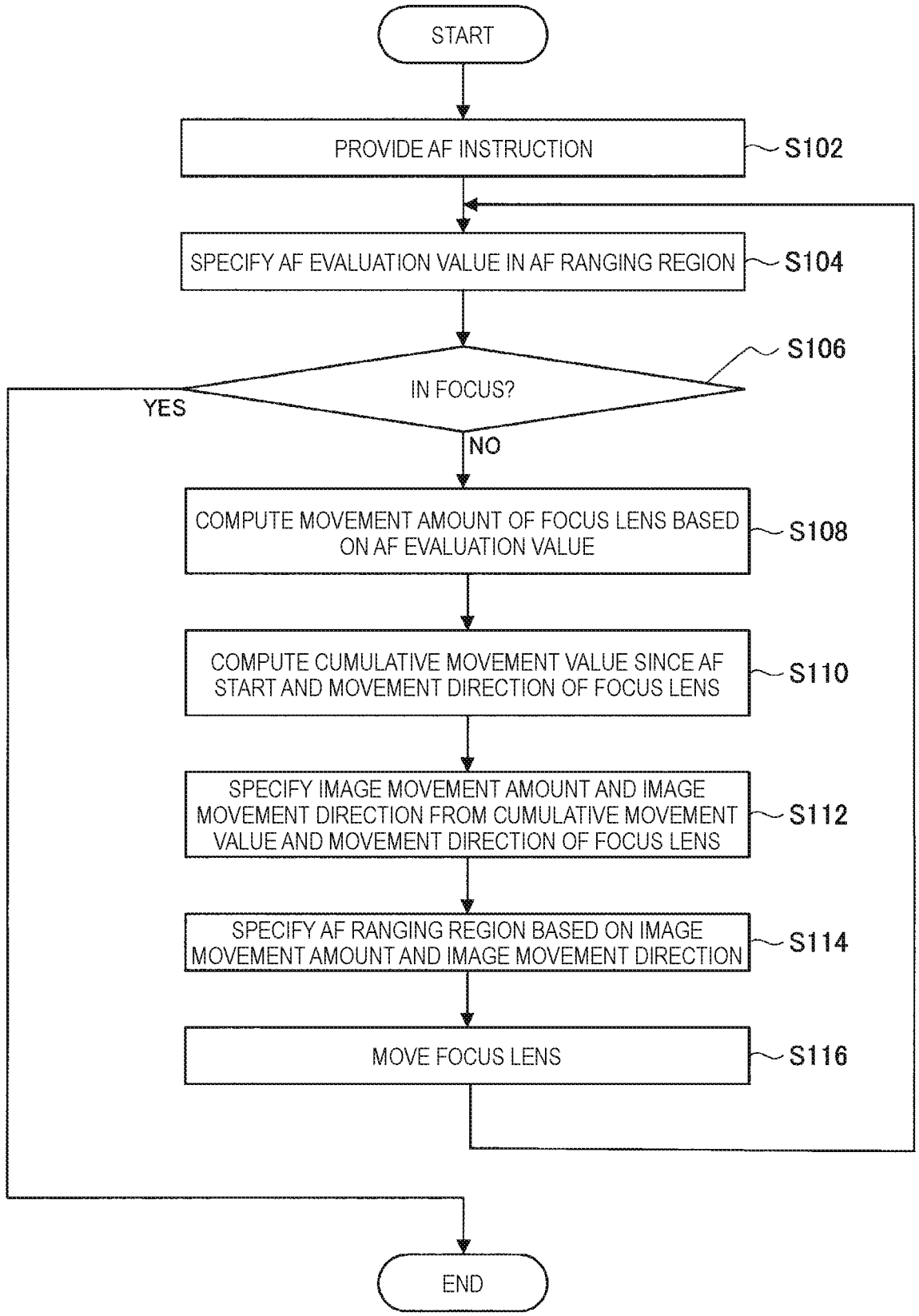
FIG. 9 is a flowchart illustrating exemplary operations of the present embodiment.

The above describes an exemplary configuration of the present embodiment. Next, exemplary operations of the present embodiment will be described with reference to FIG. 9. FIG. 9 is a flowchart illustrating exemplary operations of the present embodiment. Note that FIG. 9 mainly illustrates processes that relate to the AF operation control method by the control unit 240 from among the processes according to the present embodiment.

First, as illustrated in FIG. 9, an AF instruction signal is input by the user, and an AF operation is started by the control unit 240 (S102). Next, an AF evaluation value for the AF ranging region is specified (S104). Note that the AF ranging region immediately after starting AF may be a predetermined region set in advance for example, and an AF evaluation value may be specified on the basis of the AF ranging region.

Next, on the basis of the AF evaluation value, it is determined whether or not an in-focus state is achieved (S106). In the case of determining that an in-focus state is achieved (YES in step S106), the movement of the focus lens 102 stops, and the AF operation ends.

On the other hand, in the case of determining that an in-focus state is not achieved (NO in S106), the movement amount of the focus lens 102 is computed on the basis of the AF evaluation value (S108).

Next, on the basis of the movement amount computed in step S108, the cumulative movement value of the focus lens 102 since the start of the AF operation (one example of the movement amount) and the movement direction are computed (S110). Furthermore, the image movement amount and the image movement direction are specified on the basis of the cumulative movement value and the movement direction of the focus lens 102 (S112).

Furthermore, the AF ranging region is specified on the basis of the image movement amount and the image movement direction (S114). Next, the driving of the focus lens driving unit 107 is controlled by the focus lens driving control unit to move the focus lens 102 (SI 16).

Next, as illustrated in FIG. 9, the process returns to step S104, and an AF evaluation value is specified for the AF ranging region specified in step S114.

By repeatedly executing the series of processes described above, the AF operation is executed. Note that the operations illustrated in FIG. 9 are one example, and the present embodiment is not limited to such an example. For example, the movement of the focus lens 102 may also be performed at any point in time after step S108 until step S116.

4. Modifications

The above describes one embodiment of the present disclosure. Hereinafter, several modifications of one embodiment of the present disclosure will be described. Note that each of the modifications described hereinafter may be applied to an embodiment of the present disclosure individually, or applied to an embodiment of the present disclosure in combination with each other. Also, each modification may be applied as a substitute for the configuration described in an embodiment of the present disclosure, or applied in addition to the configuration described in an embodiment of the present disclosure.

<4-1. Modification 1>

In the foregoing embodiment, an example in which the contrast method is used as the AF method is described, but another AF method may also be used. In the following, a case in which another AF method is used will be described as Modification 1.

(Case of Using Phase Difference Method)

The case in which the phase difference method is used as the AF method in the medical observation device 1 illustrated in FIG. 7 will be described. The phase difference method is a method of performing a focusing operation by computing the distance to the subject on the basis of an image interval between two subject images obtained by causing observation light to be formed into an image at different positions on the photosensitive face, and moving the focus lens 102 such that the focal point is aligned with the subject on the basis of the computed distance to the subject.

An imaging system in which the phase difference method is applied as the AF method corresponds to a change of the functions related to AF operations in the control unit 240 in the configuration of the medical observation device 1 illustrated in FIG. 7. Specifically, in an imaging system in which the phase difference method is applied, for example, the control unit 240 illustrated in FIG. 7 executes, as processes related to AF operations, a process of acquiring the image interval between the function two subject images, a process of computing the distance to the subject on the basis of the image interval, and a process of computing the movement amount of the focus lens 102 to an in-focus position with respect to the subject on the basis of the computed distance to the subject.

Note that in the case in which the phase difference method is used, inside the imaging device 10, another image sensor for ranging may be provided separately from the image sensor 105 used for taking images, and AF operations may be performed on the basis of two subject images obtained by the other image sensor. Alternatively, a region to use for ranging may be secured in a part of the photosensitive face of the image sensor 105, and AF operations may be performed on the basis of two subject images obtained on the photosensitive face corresponding to the region to use for ranging. In this case, since taking an image of the subject and ranging for AF operations both may be performed by a single image sensor 105, the configuration of the imaging device 10 can be simplified.

(Case of Using Depth Map Method)

The case in which what is called the depth map method is used as the AF method in the medical observation device 1 illustrated in FIG. 7 will be described. The depth map method is an AF method using spatial recognition technology, and is a method of performing a focusing operation by computing the distance to the subject on the basis of the degree of blur (degree of defocus) in a subject image, and moving the focus lens 102 such that the focal point is aligned with the subject on the basis of the computed distance to the subject.

An imaging system in which the depth map method is applied as the AF method corresponds to a change of the functions related to AF operations in the control unit 240 in the configuration of the medical observation device 1 illustrated in FIG. 7. Specifically, in an imaging system in which the depth map method is applied, for example, the control unit 240 illustrated in FIG. 7 executes, as processes related to AF operations, a process of detecting the degree of defocus in a subject image, a process of computing the distance to the subject on the basis of the detected degree of defocus in the subject image, and a process of computing the movement amount of the focus lens 102 to an in-focus position with respect to the subject on the basis of the computed distance to the subject.

(Case of Using Triangle Ranging Method)

The case in which what is called the triangle ranging method is used as the AF method in the medical observation device 1 illustrated in FIG. 7 will be described. The triangle ranging method is an AF method using 3D stereogram technology, and is a method of performing a focusing operation by computing the distance to the subject according to the principle of triangulation on the basis of parallax information obtained from two subject images obtained by causing observation light to be formed into an image at different positions on the photosensitive face, and moving the focus lens 102 such that the focal point is aligned with the subject on the basis of the computed distance to the subject.

An imaging system in which the triangle ranging method is applied as the AF method corresponds to a change of the functions related to AF operations in the control unit 240 in the configuration of the medical observation device 1 illustrated in FIG. 7. Specifically, in an imaging system in which the triangle ranging method is applied, for example, the control unit 240 illustrated in FIG. 7 executes, as processes related to AF operations, a process of acquiring parallax information from two subject images, a process of computing the distance to the subject on the basis of the principle of triangulation on the basis of the parallax information and a baseline distance (the distance between the photosensors corresponding to the image-forming positions of the two subject images), and a process of computing the movement amount of the focus lens 102 to an in-focus position with respect to the subject on the basis of the computed distance to the subject.

Note that in the case in which the triangle ranging method is used, inside the imaging device 10, another image sensor for ranging may be provided separately from the image sensor 105 used for taking images, and AF operations may be performed on the basis of two subject images obtained by the other image sensor. Alternatively, a region to use for ranging may be secured in a part of the photosensitive face of the image sensor 105, and AF operations may be performed on the basis of two subject images obtained on the photosensitive face corresponding to the region to use for ranging. In this case, since taking an image of the subject and ranging for AF operations both may be performed by a single image sensor 105, the configuration of the imaging device 10 can be simplified.

<4-2. Modification 2>

The foregoing embodiment describes an example in which information related to an image movement (the image movement amount and the image movement direction) are used to control AF operations, but the present embodiment is not limited to such an example. For example, information related to the image movement specified by the control unit 240 may also be used in the signal processing by the imaging signal processing unit 210.

For example, the imaging signal processing unit 210 illustrated in FIG. 7 may shift (move) the image used for display on the basis of information related to image movement. Particularly, in the case of presenting a 2D display in which only the image signal (R) or the image signal (L) output from the imaging signal processing unit 210 is used for display, by shifting the entire image on the basis of information related to image movement for example, it becomes possible to observe the subject (observation target) in the center of the image.

5. Hardware Configuration

Figure 10:
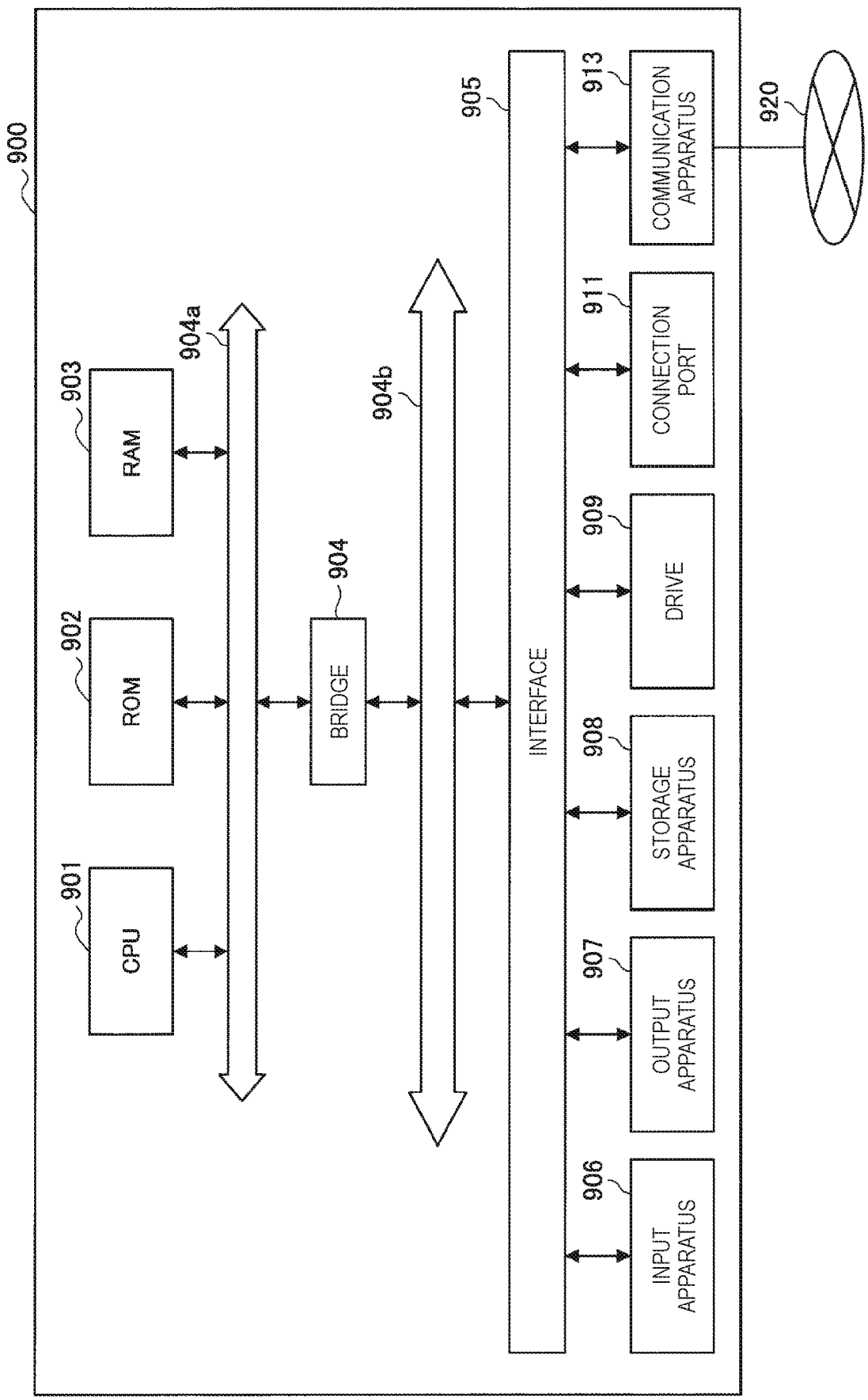
FIG. 10 is an explanatory diagram illustrating an exemplary hardware configuration.

The embodiment of the present disclosure has been described above. Last of all, with reference to FIG. 10, a hardware configuration of the information processing device according to the present embodiment will be described. FIG. 10 is a block diagram illustrating an example of a hardware configuration of the information processing apparatus according to the present embodiment. Note that the information processing apparatus 90X) illustrated in FIG. 10 may realize the medical observation device 1 and the control device 20, for example. Information processing by the medical observation device 1 and the control device 20 according to the present embodiment may also be realized by cooperative action between software and the hardware described below.

As illustrated in FIG. 10, the information processing apparatus 900 includes a central processing unit (CPU) 901, read only memory (ROM) 902, random access memory (RAM) 903, and a host bus 904a. In addition, the information processing apparatus 900 includes a bridge 904, an external bus 904b, an interface 905, an input apparatus 906, an output apparatus 907, a storage apparatus 908, a drive 909, a connection port 911, a communication apparatus 913, and a sensor 915. The information processing apparatus 900 may include a processing circuit such as a DSP or an ASIC instead of or in addition to the CPU 901.

The CPU 901 functions as an arithmetic processing apparatus and a control apparatus to control entire operation in the information processing apparatus 900 in accordance with various kinds of programs. The CPU 901 may be a microprocessor. The ROM 902 stores programs, arithmetic parameters, and the like used by the CPU 901. The RAM 903 transiently stores programs used when the CPU 901 is executed, various parameters that change as appropriate when executing such programs, and the like. The CPU 901 may be configured as the control unit 240, for example.

The CPU 901, the ROM 902, and the RAM 903 are connected to each other through the host bus 904a including a CPU bus and the like. The host bus 904a is connected, via the bridge 904, to the external bus 904b such as a peripheral component interconnect/interface (PCI) bus. Note that, the host bus 904a, the bridge 904, and the external bus 904b are not necessarily configured as a separate component. Their functions may be incorporated into in a single bus.

The input apparatus 906 is implemented as an apparatus allowing the user to input information, such as a mouse, a keyboard, a touchscreen, a button, a microphone, a switch, and a lever. In addition, the input apparatus 906 may be a remote controller using infrared ray or other electric waves, or may be an external connection device such as a cellular phone or a PDA that correspond to operation performed on the information processing apparatus 900, for example. Furthermore, the input apparatus 906 may include an input control circuit or the like that is configured to generate an input signal on the basis of information input by the user using the aforementioned input mechanism and output the generated input signal to the CPU 901. The user of the information processing apparatus 900 is capable of inputting various types of data to the information processing apparatus 900, or instructing the information processing apparatus 900 to perform process operation, by operating the input apparatus 906.

The output apparatus 907 is configured as an apparatus capable of issuing a visual or auditory notification of the acquired information to the user. Examples of such an apparatus include a display apparatus such as a CRT display apparatus, a liquid crystal display apparatus, a plasma display apparatus, an EL display apparatus, or a lamp, a sound output apparatus such as a speaker or a headphone, a printer apparatus, and the like. The output apparatus 907 outputs, for example, results acquired by various processes performed by the information processing apparatus 900. Specifically, the display apparatus visually displays results acquired by various processes performed by the information processing apparatus 900 in various formats such as text, images, tables, and graphs. On the other hand, the sound output apparatus converts audio signals including reproduced sound data, audio data, and the like into analog signals and audibly outputs the analog signals.

The storage apparatus 908 is a data storage apparatus configured as an example of the storage unit of the information processing apparatus 900. For example, the storage apparatus 908 is implemented as a magnetic storage device such as an HDD, a semiconductor storage device, an optical storage device, a magneto-optical storage device, or the like. The storage apparatus 908 may include a storage medium, a recording apparatus for recording data on the storage medium, a reading apparatus for reading data from the storage medium, a deletion apparatus for deleting data recorded on the storage medium, and the like. The storage apparatus 908 stores programs and various types of data executed by the CPU 901, various types of data acquired from the outside, and the like. The storage apparatus 908 may be configured as the storage unit 250, for example.

The drive 909 is a reader/writer for a storage medium, and is incorporated in or externally attached to the information processing apparatus 900. The drive 909 reads information recorded on a removable recording medium that is mounted such as a magnetic disk, an optical disc, a magneto-optical disk, or semiconductor memory, and outputs the information to the RAM 903. In addition, the drive 909 is also capable of writing information to the removable storage medium.

The communication port 911 is an interface for connection to an external device, and is, for example, a connection port for connection to an external device capable of transmitting data via a Universal Serial Bus (USB).

The communication apparatus 913 is, for example, a communication interface configured as a communication device or the like for connection with a network 920. The communication apparatus 913 is, for example, a communication card or the like for a wired or wireless local area network (LAN), long term evolution (LTE), Bluetooth (registered trademark), or wireless USB (WUSB). In addition, the communication apparatus 913 may be a router for optical communication, a router for asymmetric digital subscriber line (ADSL), a modem for various communication, or the like. For example, the communication apparatus 913 is capable of transmitting and receiving signals and the like to and from the Internet or other communication devices, for example, in accordance with a predetermined protocol such as TCP/IP or the like.

Note that, the network 920 is a wired or wireless communication path through which information is transmitted from apparatuses connected to the network 920. The network 920 may include a public network such as the Internet, a telephone network, and a satellite communication network, various local area networks (LANs) including Ethernet (registered trademark), a wide area network (WAN), and the like. In addition, the network 920 may include a dedicated network such as an internet protocol-virtual private network (IP-VPN).

The example of a hardware configuration capable of achieving the functions of the information processing apparatus 900 according to the present embodiment has been described above. The respective structural elements described above may be implemented using universal members, or may be implemented by hardware that is specific to the functions of each of the structural elements. Accordingly, it is possible to change a hardware configuration to be used appropriately depending on the technical level at each time of carrying out the present embodiment.

Note that, a computer program for implementing each of the functions of the information processing apparatus 900 according to the present embodiment may be created, and may be mounted in a PC or the like. Furthermore, a computer-readable recording medium on which such computer programs are stored may be provided. The recording medium is, for example, a magnetic disc, an optical disc, a magneto-optical disc, a flash memory, or the like. The computer program may be distributed, for example, through a network without using the recording medium.

6. Conclusion

As described above, according to an embodiment of the present disclosure, in an observation device provided with an imaging optical system that includes a single objective lens and an optical system which has an optical axis different from the optical axis of the objective lens and which causes light condensed by the objective lens to form an image, it is possible to realize an autofocus function.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the foregoing embodiment describes an example in which the imaging optical system includes an image-forming optical system for the right eye and for the left eye, but the present technology is not limited to such an example. For example, the imaging optical system may include a greater number of image-forming optical systems having optical axes different from the optical axis of the objective optical system, or include only a single image-forming optical system.

Also, the foregoing embodiment describes an example in which the present technology is applied to a medical observation system including a video microscope device as the medical observation device, but the present technology is not limited to such an example. For example, the present technology is also applicable to an endoscopic system. In such a case, the imaging device 10 described with reference to FIG. 7 may correspond to a camera head of the endoscopic system, and the control device 20 may correspond to a camera control unit (CCU) of the endoscopic system.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A medical observation device including:
an imaging optical system including an objective optical system that condenses light from a subject and two image-forming optical systems which have optical axes different from an optical axis of the objective optical system and which cause light condensed by the objective optical system to form an image; and
a control unit configured to cause an autofocus operation to be executed by causing a focusing optical member included in the objective optical system to move.

(2)
The medical observation device according to (1), in which
the control unit specifies a ranging region for the autofocus operation on the basis of a position or a movement amount of the focusing optical member.

(3)
The medical observation device according to (2), in which
the control unit specifies an image movement direction and an image movement amount of a subject image associated with the autofocus operation on the basis of the position or the movement amount of the focusing optical member, and specifies the ranging region on the basis of the image movement direction and the image movement amount.

(4)
The medical observation device according to (3), in which
the control unit further causes a zoom operation to be executed by causing a zooming optical member included in the two image-forming optical systems to move, and specifies the image movement direction and the image movement amount further on the basis of information related to the zoom operation.

(5)
The medical observation device according to (4), in which
the control unit specifies the image movement amount on the basis of a data table associating information related to the zoom operation with the image movement direction and the image movement amount in a case of moving the focusing optical member in a predetermined direction by a predetermined amount.

(6)
The medical observation device according to (4) or (5), in which the information related to the zoom operation includes either one of a focal length of the image-forming optical systems or a magnification of the image-forming optical systems.

(7)
The medical observation device according to any one of (3) to (6), further including:
an imaging signal processing unit configured to execute signal processing on the basis of the image movement direction or the image movement amount.

(8)
A control method, executed by a processor, including:
causing an autofocus operation to be executed by causing a focusing optical member included in an objective optical system to move in an imaging optical system including the objective optical system that condenses light from a subject and two image-forming optical systems which have optical axes different from an optical axis of the objective optical system and which cause light condensed by the objective optical system to form an image.

REFERENCE SIGNS LIST 1 medical observation device
10 imaging device
20 control device
101 imaging optical system
102 focus lens
103 zoom lens
105 image sensor
107 focus lens driving unit
111 zoom lens driving unit
115 image sensor driving unit
210 imaging signal processing unit
240 control unit
241 ranging gate unit
243 ranging unit
245 focus lens movement amount decision unit
247 ranging region specification unit
249 zoom operation control unit
250 storage unit

The invention claimed is:
1. A medical observation device comprising:
an imaging optical system including an objective optical system that condenses light from a subject and two image-forming optical systems which have optical axes different from an optical axis of the objective optical system and which cause light condensed by the objective optical system to form an image; and
control circuitry configured to cause an autofocus operation to be executed by causing a focusing optical member included in the objective optical system to move and cause a zoom operation to be executed by causing a zooming optical member included in the two image-forming optical systems to move, wherein
the control circuitry specifies an image movement direction and an image movement amount of a subject image caused by the movement of the focusing optical member on a basis of (1) information related to the zoom operation including a focal length of the two image-forming optical systems or a magnification of the two image-forming optical systems and (2) a position or a movement amount of the moved focusing optical member, and specifies a ranging region for the autofocus operation on a basis of the specified image movement direction and the specified image movement amount, and the control circuitry specifies the image movement amount on a basis of data associating information related to the zoom operation with the image movement direction and the image movement amount.

2. The medical observation device according to claim 1, further comprising:

imaging signal processing circuitry configured to execute signal processing on a basis of the image movement direction or the image movement amount.

3. The medical observation device according to claim 1, wherein the data is a data table associating the information related to the zoom operation with the image movement direction and the image movement amount in a case of moving the focusing optical member in a predetermined direction by a predetermined amount.

4. The medical observation device according to claim 1, wherein the data is formula.

5. A control method, executed by a processor, comprising:

causing an autofocus operation to be executed by causing a focusing optical member included in an objective optical system to move and causing a zoom operation to be executed by causing a zooming optical member included in the two image-forming optical systems to move, in an imaging optical system including the objective optical system that condenses light from a subject and two image-forming optical systems which have optical axes different from an optical axis of the objective optical system and which cause light condensed by the objective optical system to form an image, wherein an image movement direction and an image movement amount of a subject image caused by the movement of the focusing optical member are specified on a basis of (1) information related to the zoom operation including a focal length of the two image-forming optical systems or a magnification of the two image-forming optical systems and (2) a position or a movement amount of the moved focusing optical member, and a ranging region for the autofocus operation is specified on a basis of the specified image movement direction and the specified image movement amount, and the image movement amount is specified on a basis of data associating information related to the zoom operation with the image movement direction and the image movement amount in a case of moving the focusing optical member in a predetermined direction by a predetermined amount.

6. The control method according to claim 5, wherein the data is a data table associating the information related to the zoom operation with the image movement direction and the image movement amount in a case of moving the focusing optical member in a predetermined direction by a predetermined amount.

7. The control method according to claim 5, wherein the data is formula.

* * * * *